United States Patent [19]

Eidt et al.

[11] Patent Number: 4,841,082
[45] Date of Patent: Jun. 20, 1989

[54] PREPARATION OF DIMETHYLZINC

[75] Inventors: Scott H. Eidt; Dennis L. Deavenport, both of Seabrook; Nam H. Tran, Houston, all of Tex.

[73] Assignee: Texas Alkyls, Inc., Deer Park, Tex.

[21] Appl. No.: 233,774

[22] Filed: Aug. 19, 1988

[51] Int. Cl.⁴ .............................................. C07F 3/06
[52] U.S. Cl. .................................................... 556/129
[58] Field of Search .......................................... 556/129

[56] References Cited

U.S. PATENT DOCUMENTS 4,670,571  6/1987  Malpass et al. ..................... 556/129

Primary Examiner—Donald B. Moyer
Assistant Examiner—Stuart L. Hendrickson
Attorney, Agent, or Firm—Richard P. Fennelly; Louis A. Morris

[57] ABSTRACT

Dimethylzinc is prepared by heating a dimethylaluminum halide, e.g., dimethylaluminum chloride, and a dialkylzinc, e.g., diethylzinc, with distillative removal of dimethylzinc from the reaction mixture which results therefrom.

5 Claims, No Drawings

PREPARATION OF DIMETHYLZINC

BACKGROUND OF THE INVENTION

1. Field of the Invention

The present invention relates to a novel process for the manufacture of dimethylzinc.

2. Description of the Prior Art

Dimethylzinc finds current utility as a dopant for compound semiconductors. A variety of processes for its manufacture have been described. "Comprehensive Organometallic Chemistry", Vol. 2, G. Wilkinson, ed., at pages 832–833 lists several approaches that can be used: the direct reaction of metallic zinc with organic halides; the alkylation or arylation of zinc salts, such as zinc chloride or zinc acetate using an organomagnesium, organolithium, or organoaluminum compound; and transmetallation reactions, e.g., reaction of zinc metal with an organomercury compound.

It is known from "Organoaluminium Compounds", by T. Mole et al., p. 337, and "J. Gen. Chem. USSR", Eng. Transl. 30 (1960) 2109–2112, that trimethylaluminum undergoes rapid redistribution with such zinc alkyls as diethylzinc and dipropylzinc to yield dimethylzinc in about 50%–60% yield upon distillation of the more volatile component.

SUMMARY OF PRESENT INVENTION

The present invention is based upon the discovery that the heating of a dimethylaluminum halide with a dialkylzinc allows for production of the desired dimehylzinc, which is distillatively removed from the resulting reaction medium in good yield. The instant reaction is unexpected in view of the weaker alkylating characteristics of dimethylaluminum halides as compared to trialkylaluminums.

DETAILED DESCRIPTION OF THE PRESENT INVENTION

The dimethylaluminum halide reagent used in the instant process can be from any source. However, in a preferred embodiment, this reagent is dimethylaluminum chloride and is a by-product resulting from the production of trimethylgallium involving the reaction of gallium trichloride with trimethylaluminum as described by J. J. Eisch in J. Amer. Chem. Soc. 84(19), 3605–3610 (1962). Therefore, the instant process has the additional advantage of using a production by-product as a starting reagent ot make a very desirable organozinc compound.

The relative molar ratio of the dimethylaluminum halide reagent to dialkylzinc reagent used in the instant process can range from about 1.25:1.0 to about 1.0:1.25. The boiling point of dimethylzinc product from the reaction is 44° C. and is the driving force in insuring distillative removal from the reaction mixture after the redistribution reaction between the dimethylaluminum halide, e.g., dimethylaluminum chloride (b.p.=126° C.) and dialkylzinc, e.g., diethylzinc (b.p.=118° C.). It is contemplated by the instant invention that the dialkylzinc species which can be used include not only diethylzinc (which is shown in the Examples which follow) but other, higher boiling, dialkylzinc compounds including n- and i-propyl, n- and i-butyl, etc. The dimethylaluminum halides which can be used, besides dimethylaluminum chloride, also include the corresponding bromide compound. The reaction mixture is heated to a sufficiently high temperature (100°–150° C. at atmospheric pressure) to insure removal of the desired dimethylzinc from the reaction mixture. The reaction is conducted under an inert atmosphere (e.g., nitrogen), and yields of 75%–85% have been achieved.

The instant process is further illustrated by the Examples which follow.

EXAMPLE 1

Dimethylaluminum chloride (DMAC) (181.9 grams, 1.966 moles) was charged under nitrogen to a flask fitted with a fractional distillation column. After heating DMAC to 90° C., 274.4 grams (2.222 moles) of diethylzinc (DEZ) was slowly added. Distillation of DMZ boiling at 44° C. at atmospheric pressure was continued until it stopped coming over. Based on the limiting reagent, the dimethylzinc (DMZ) collected (158.7 grams, 1.663 moles) represented a yield of 84.6%.

EXAMPLE 2

Dimethylaluminum chloride (1,500 grams, 16.22 moles) was charged under nitrogen to a flask fitted with a fractional distillation column. After heating DMAC to 110° C., (1,990 grams 16.13 moles) of DEZ were slowly added. DMZ was distilled at atmospheric pressure until the distillation rate slowed. The pressure was gradually reduced to 500 torr and distillation was continued until the vapor temperature started to rise. Recovered DMZ (850 milliliters, 1,156 grams, 12.11 moles) represented a 75% yield.

The foregoing Examples should merely be taken as illustrative of certain embodiments of the present invention and should not, therefore, be construed in a limiting sense. The scope of protection which is sought is set forth in the claims which follow.

We claim:

1. A process for the preparation of dimethylzinc which comprises heating a dimethylaluminum halide and a dialkylzinc under an inert atmosphere to achieve a redistribution reaction between the dimethylaluminum halide and dialkylzinc with distillative removal of the lower boiling dimethylzinc from the resulting reaction mixture wherein the alkyl groups are lower alkyl and the dialkylzinc is not dimethylzinc.

2. A process as claimed in claim 1 wherein the dimethylaluminum halide is dimethylaluminum chloride.

3. A process as claimed in claim 1 wherein the dialkylzinc is diethylzinc.

4. A process as claimed in claim 1 wherein the molar ratio of dimethylaluminum halide to dialkylzinc is from about 1.25:1.0 to about 1.0:1.25.

5. A process as claimed in claim 1 wherein dimethylaluminum chloride and diethylzinc are reacted.

* * * * *